United States Patent [19]

George et al.

[11] Patent Number: 4,978,028
[45] Date of Patent: Dec. 18, 1990

[54] DISPOSABLE BIOHAZARDOUS WASTE MATERIAL CONTAINER

[75] Inventors: John W. George; Laurence D. Taylor, both of Erie, Pa.

[73] Assignee: American Sterilizer Company, Erie, Pa.

[21] Appl. No.: 300,677

[22] Filed: Jan. 23, 1989

[51] Int. Cl.⁵ .............................................. B65D 25/00
[52] U.S. Cl. .................................... 220/403; 220/408; 220/1 T
[58] Field of Search ............... 220/403, 404, 408, 400, 220/402, 441, 461, 1 T

[56] References Cited

U.S. PATENT DOCUMENTS

| | | | |
|---|---|---|---|
| 3,539,360 | 11/1970 | Wood | 220/403 X |
| 3,734,340 | 5/1973 | Ippolito et al. | 220/402 |
| 3,741,434 | 6/1973 | Traverse | 220/1 T X |
| 3,762,599 | 10/1973 | Bourgeois | 220/402 |
| 3,917,107 | 11/1975 | Bottas et al. | 220/402 |
| 4,534,489 | 8/1985 | Bartlett | 220/1 T X |
| 4,552,720 | 11/1985 | Baker, Sr. et al. | |
| 4,662,516 | 5/1987 | Baker, Sr. et al. | |
| 4,742,951 | 5/1988 | Kelly et al. | 220/408 X |

OTHER PUBLICATIONS

Undated advertisement for Biohazardous Material Disposal Service.

Primary Examiner—Steven M. Pollard
Attorney, Agent, or Firm—Kirkpatrick & Lockhart

[57] ABSTRACT

A disposable container for the handling of biohazardous waste material includes a substantially rectangular six-sided exterior box, a polyethylene liner receivable within the exterior box, a substantially rectangular four-sided interior insert positioned within the liner and a substantially rectangular inner box bottom positioned within the interior insert. The exterior box includes two top flaps and two lid sections each of which is integral with and in a hinged relationship with one of the sides of the exterior box. The top flaps and lid sections form a closure at the top portion of the exterior box. One of the top flaps includes an access hole for dropping waste material into the disposable container. The interior insert includes end flaps at the top and bottom of each of the sides integral with and in a hinged relationship with each of the sides of the interior insert to maintain the interior insert in a stable and equidistant relationship with respect to each of the sides of the exterior box. The inner box bottom includes a center beam positioned normal to the top and bottom of the inner box bottom and parallel to each of the sides of the inner box bottom.

6 Claims, 2 Drawing Sheets

DISPOSABLE BIOHAZARDOUS WASTE MATERIAL CONTAINER

BACKGROUND OF THE INVENTION

1. Field of the Invention

The present invention relates to the handling of biohazardous waste material and more particularly to disposable containers for the handling of biohazardous waste material.

2. Description of the Prior Art

In any medical facility, the disposal of contaminated syringes and other medical devices is a problem of great concern. The interest of protecting the general populace from the spreading of certain virulent diseases requires that contaminated medical devices be disposed of in a manner which will eliminate the possibility that the community will be exposed to any such diseases. An additional interest involves preventing those engaged in the illegal drug business from recovering used syringes for illicit purposes. Thus, there are two concerns in any disposal procedure, i.e., the clinical concern for limiting unwanted contamination and spread of disease and the concern over unauthorized use of medical devices.

Apparatus and techniques exist for the disposal of contaminated syringes and other medical equipment. One such device is disclosed in U.S. Pat. No. 4,662,516 wherein a wall unit is provided for receiving, through a convolved opening, medical debris. The medical debris is collected within a thermoplastic liner which is periodically removed from the unit and heated in the course of sterilization to melt the top and bottom surfaces of the liner around the debris. This device requires that the thermoplastic liner containing the medical debris be subjected to the sterilization process prior to disposal by incineration or by other means. It is desirable, however, from the standpoint of efficiency, to employ a method of disposing of contaminated medical equipment which does not require sterilization prior to disposal.

It is apparent, therefore, that the need exists for a device which may be used to effectively dispose of contaminated medical equipment without sterilization in such a way as to contain any virulent diseases and at the same time to destroy the functional capabilities of the medical equipment.

SUMMARY OF THE INVENTION

The present invention is directed to a disposable container for the handling of biohazardous waste material comprised of an exterior box having sides, a bottom and an openable and closable top which together define a cavity, a polyethylene liner having an open top which is receivable within the exterior box, an interior insert having sides which are each parallel to and of similar dimensions to one side of the exterior box positioned within the polyethylene liner and an inner box bottom positioned within the bottom of the interior insert. The exterior box, interior insert and inner box bottom are constructed from 200 pound C-Flute corrugated cardboard. The exterior box includes two top flaps and two lid sections each of which is integral with and in a hinged relationship with one of the sides of the exterior box. One of the top flaps includes an access hole for dropping waste material into the disposable container. The interior insert includes end flaps at the top and bottom of each of the sides integral with and in a hinged relationship with each of the sides of the interior insert to maintain the interior insert in a stable and equidistant relationship with respect to each of the sides of the exterior box. The inner box bottom has a top surface, a bottom surface and two parallel side surfaces and includes a center beam positioned normal to the top and bottom surfaces of the inner box bottom and parallel to each of the side surfaces of the inner box bottom. The interior insert and inner box bottom prevent puncture of the polyethylene liner and strike-through of the exterior box by sharp medical devices.

The disposable biohazardous waste material container, when full of contaminated medical devices, may be incinerated so as to contain any virulent diseases and to destroy the functional capabilities of the devices. Thus, the interest of protecting the general populace from both the spreading of virulent diseases and the recovery of used syringes for illicit purposes is satisfied. These and other details, objects and advantages of the invention will become apparent as the following description of the present preferred embodiment thereof proceeds.

BRIEF DESCRIPTION OF THE DRAWINGS

In order that the present invention may be clearly understood and readily practiced, preferred embodiments will now be described, by way of example only, with reference to the accompanying figures wherein.

DETAILED DESCRIPTION OF THE PREFERRED EMBODIMENTS

Figure 1:
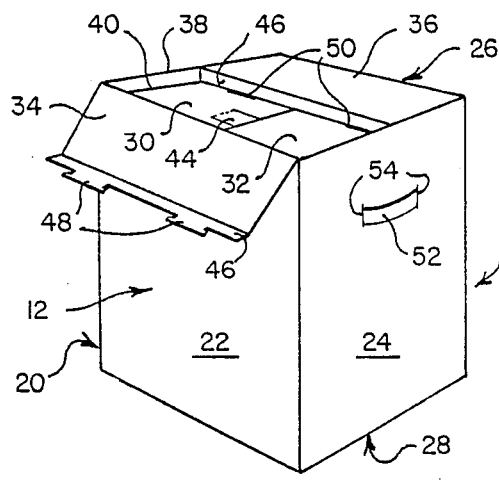
FIG. 1 illustrates in perspective view the exterior box portion of the disposable biohazardous waste material container of the present invention.
Figure 4:
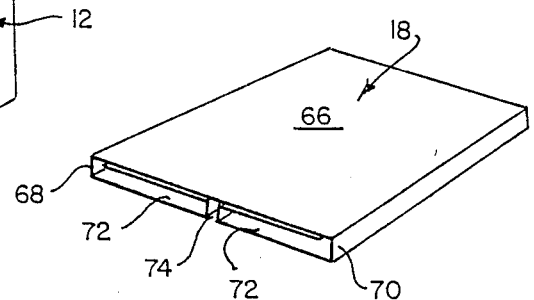
FIG. 4 illustrates in perspective view the inner box bottom portion of the disposable biohazardous waste material container of the present invention.

As illustrated in FIGS. 1 through 5, the disposable biohazardous waste material container, designated generally by the numeral 10 (FIG. 3), is comprised of an exterior box 12 of substantially rectangular construction, an interior rectangular insert 14, a plastic liner 16 situated between exterior box 12 and interior rectangular insert 14, and inner box bottom 18 (FIG. 4). The exterior box 12, shown in FIG. 1, is constructed of a single piece of 200 pound C-Flute corrugated cardboard and, when assembled, consists of four sides 20, 22, 24 and 26, bottom 28, top flaps 30 and 32 and lid sections 34 and 36. Each of sides 22 and 26 may have a height of 24 inches and a width of $18\frac{1}{8}$ inches. Each of sides 20 and 24 may have a height of 24 inches and a width of 15 inches. Bottom 28 may have a width of 15 inches and a length of $18\frac{1}{8}$ inches. Each of top flaps 30 and 32 may have a width of 9 1/16 inches and a length of 15 inches while each of lid sections 34 and 36 may have a width of $7\frac{1}{2}$ inches and a length of $18\frac{1}{8}$ inches. The exterior box 12 is assembled by the well-known method of gluing on one of the four sides 20, 22, 24 or 26 and by the well-known method of cutting the portions of the single piece of cardboard which form the bottom 28 so that the portions are interlocking.

Top flap edge 38 is perforated and serves to both provide a hinged relationship between side 20 and top flap 30 and also to permit top flap 30 to be removed from the exterior box 12 if desired. Top flap edge 40 is also perforated and serves to provide a recess in height between top flap 30 and lid sections 34 and 36. Top flap 32 is constructed in an identical manner to top flap 30. Access hole 42 is formed in top flap 30 by cutting three sides of access hole flap 44 into top flap 30 as shown. Lid sections 34 and 36, each of which is integral with and in a hinged relationship with sides 22 and 26, respectively, are provided with end flaps 46 and locking tabs 48. Locking tabs 48 can be inserted into tab slots 50, one of which is cut into each of top flaps 30 and 32. A handle 52 constructed of semi-rigid plastic is located on each of sides 20 and 24. Each handle has two end tabs (not shown) which are inserted into end tab slots 54 cut into sides 20 and 24 of exterior box 12.

Figure 2:
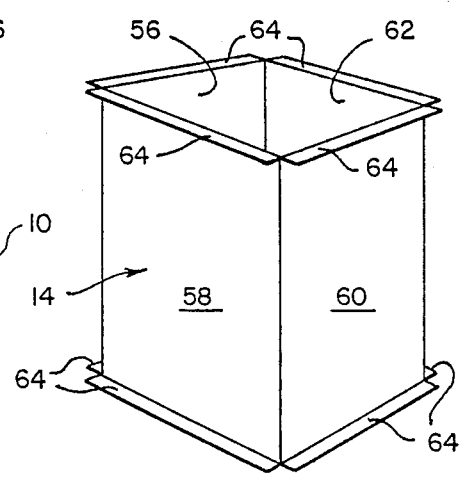
FIG. 2 illustrates in perspective view the interior rectangular insert portion of the disposable biohazardous waste material container of the present invention.
Figure 3:
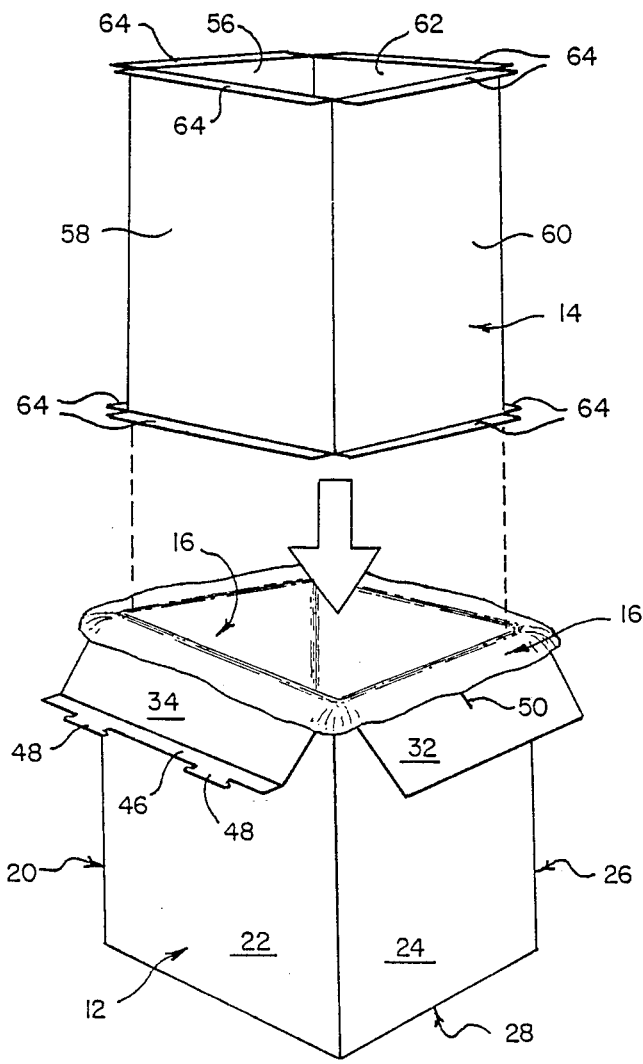
FIG. 3 illustrates in perspective view the way in which the device illustrated in FIG. 2 is used in conjunction with the device illustrated in FIG. 1.

FIG. 2 illustrates interior rectangular insert 14 which is also constructed of a single piece of 200 pound C-Flute corrugated cardboard. When assembled by gluing, interior rectangular insert 14 consists of four sides 56, 58, 60 and 62 each of which has a spacer flap 64 located at its top and bottom. Spacer flaps 64 may have a width of 1¼ inches. Each of the four sides 56, 58, 60 and 62 of interior rectangular insert 14 may have a height of 24 inches. Sides 58 and 62 may have a width of 15⅝ inches while sides 56 and 60 may have a width of 12½ inches. The spacer flaps 64 are integral with and in a hinged relationship with each of the four sides 56, 58, 60 and 62. The spacer flaps 64 serve to maintain interior rectangular insert 14 in a stable and equidistant relationship with respect to each of the sides 20, 22, 24 and 26 of exterior box 12 when interior rectangular insert 14 is inserted into plastic liner 16 as shown in FIG. 3. Any means functionally equivalent to the spacer flaps 64 such as styrofoam, wooden blocks, etc. which will maintain rectangular insert 14 in its spaced relationship with respect to exterior box 12 may be substituted for spacer flaps 64.

Plastic liner 16, illustrated in FIG. 3, is constructed of polyethylene with a minimum thickness of 40 mils and is of sufficient size to completely line exterior box 12 and extend for several inches beyond the top of each of the sides 20, 22, 24 and 26. Plastic liner 16 is glued to the interior portion of each of sides 20, 22, 24 and 26 of exterior box 12 at a position on each side 20, 22, 24 and 26 approximately one-third of the distance from the top to bottom of each side 20, 22, 24 and 26 of exterior box 12. The top edge of plastic liner 16 may be folded over and fixed in this position in order to form a channel (not shown) for receiving a drawstring (not shown).

Figure 5:
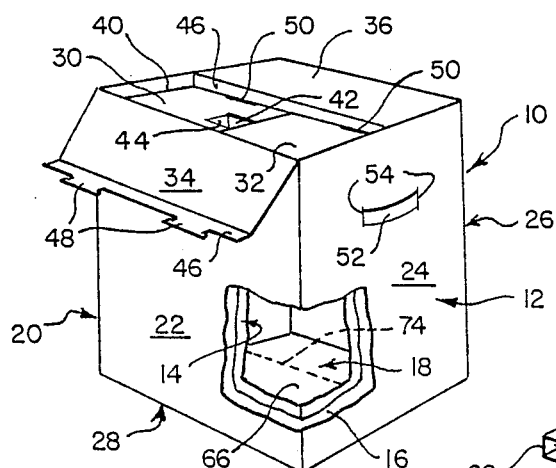
FIG. 5 illustrates in perspective view a cut-away representation of the completely assembled disposable biohazardous waste material container of the present invention.

Inner box bottom 18, illustrated in FIG. 4 and rotated 90° in perspective in relation to the other drawings, is formed from a single sheet of 200 pound C-Flute corrugated cardboard. The cardboard is folded and glued in order to form the three-dimensional rectangular inner box bottom 18 with a double layer of cardboard at its top 66 and a single layer of cardboard at each of its sides 68 and 70 and at its bottom 72. As a result of this design, a double layer cardboard center beam 74 is formed. The center beam 74 is situated normal to top 66 and bottom 72 and parallel to sides 68 and 70. Inner box bottom 18 is inserted into the bottom of interior rectangular insert 14 as illustrated in FIG. 5.

In operation, the biohazardous waste material container 10 may be used in either one of two ways. In one method of use, after the interior rectangular insert 14 is inserted into the exterior box 12 as shown in FIG. 3 and the inner box bottom 18 is inserted into the bottom of interior rectangular insert 14 as shown in FIG. 5, top flaps 30 and 32 may be closed as shown in FIG. 1. Lid section 36 may also then be closed in order to maintain top flaps 30 and 32 in the closed position. Access hole flap 44 may be depressed as shown in FIG. 1 to provide access to the enclosure formed by interior rectangular insert 14 through access hole 42. Contaminated syringes and other medical devices may be discarded by dropping them through access hole 42. The biohazardous waste material container 10 may alternatively be used with both top flaps 30 and 32 in the open position. This configuration provides for the disposal of large amounts of contaminated medical equipment at any one time.

When the biohazardous waste material container 10 is full of contaminated medical equipment, the lid section 36 and top flaps 30 and 32 are opened, if they are not already in this position, and the plastic liner 16 is tied shut using portions of the liner 16 extending beyond the top of each of the exterior box sides 20, 22, 24 and 26. If a drawstring (not shown) is employed, the plastic liner 16 is closed by means of the drawstring. Top flaps 30 and 32 and lid sections 34 and 36 are then closed. The biohazardous waste material container 10 may then be transported using handles 54 to a central collection point for decontamination and destruction by incineration. The inner box bottom 18 provides the required support during transport for loads up to 50 pounds, while the double box construction provided by interior rectangular insert 14, inner box bottom 18 and plastic liner 16 in conjunction with exterior box 12 prevents strike-through of sharp debris. Moreover, sharp objects may not puncture the plastic liner 16 because it is protected on its sides by rectangular insert 14 and on its bottom by inner box bottom 18. Applicants have discovered that it is important to avoid puncturing the plastic liner 16 so that any liquids contained in the biohazardous waste material container 10 may not escape by leakage.

It will be understood that various changes in the details, materials and arrangements of parts which have been herein described and illustrated in order to explain the nature of the invention may be made by those skilled in the art within the principle and scope of the invention as expressed in the appended claims.

What is claimed is:

1. A disposable container for the handling of waste material, comprising:
   an exterior box member having sides, a bottom and an openable and closeable top which together define a cavity;
   a plastic liner having an open top and which is receivable within said cavity;
   an interior insert member positioned within said plastic liner, said insert member having sides which are each parallel to and of similar dimensions to one side of said exterior box and end flaps at the top and bottom of each of said sides of said insert member integral with and in a hinged relationship with each of said sides of said insert member to maintain said insert member in a stable and equidistant relationship with respect to each of said sides of said exterior box; and an inner box bottom positioned within the bottom of said interior insert.

2. The disposable container of claim 1 wherein said top of said exterior box includes two top flaps and two lid sections each of which is integral with and in a hinged relationship with one of said sides of said exterior box.

3. The disposable container of claim 2 wherein one of said two top flaps includes an access hole through which waste material may be inserted into the disposable container.

4. The disposable container of claim 1 wherein said inner box bottom has a top surface, a bottom surface and two parallel side surfaces and includes a center beam positioned normal to said top and bottom surfaces of said inner box bottom and parallel to each of said parallel sides of said inner box bottom.

5. The disposable container of claim 1 wherein said exterior box, said interior insert and said inner box bottom are constructed from 200 pound C-Flute corrugated cardboard.

6. The disposable container of claim 1 wherein said plastic liner is constructed of polyethylene.

* * * * *